United States Patent
Garcia Lopez et al.

(10) Patent No.: US 6,187,574 B1
(45) Date of Patent: Feb. 13, 2001

(54) **PROCESS FOR PRODUCING THE ENZYME D-AMINO ACID OXIDASE OF *RHODOTORULA GRACILIS* IN HOST CELLS**

(75) Inventors: Jose Luis Garcia Lopez; Estrella Cortes Rubio; Jorge Alonso Palacios, all of Madrid; Jose Luis Barredo Fuente, Leon; Bruno Diez Garcia, Leon; Miguel Angel Moreno Valle, Leon; Carmen Schleissner Sanchez, Leon; Alfonso Collados de la Vieja, Leon; Alejandro Vitaller Alba, Leon; Francisco Salto Maldonado, Madrid, all of (ES)

(73) Assignee: Antibiotics, S.A., Madrid (ES)

( * ) Notice: Under 35 U.S.C. 154(b), the term of this patent shall be extended for 0 days.

(21) Appl. No.: 08/973,914

(22) PCT Filed: Apr. 18, 1997

(86) PCT No.: PCT/ES97/00099
§ 371 Date: Apr. 28, 1998
§ 102(e) Date: Apr. 28, 1998

(87) PCT Pub. No.: WO97/40171
PCT Pub. Date: Oct. 30, 1997

(30) Foreign Application Priority Data

Apr. 22, 1996 (ES) .................................................. 9600906

(51) Int. Cl.[7] .............................. C12N 9/02; C07H 21/04
(52) U.S. Cl. ................ 435/189; 435/252.3; 435/252.33; 435/320.1; 536/23.1; 536/23.2
(58) Field of Search ..................................... 435/189, 191, 435/252.3, 252.33, 320.1, 254.11, 254.21; 536/23.2, 23.1, 23.74

(56) References Cited

U.S. PATENT DOCUMENTS 5,877,013 * 3/1999 Liao et al. ......................... 435/320.1
5,948,660 * 9/1999 Pilone ................................. 435/191

FOREIGN PATENT DOCUMENTS 0364275  4/1990  (EP) .
0496993  8/1992  (EP) .
0517200  12/1992  (EP) .
0583817  2/1994  (EP) .
9627667  9/1996  (WO) .

OTHER PUBLICATIONS

Kim et al. "Simple and rapid determination of the activity of Recombinant D–Amino acid oxidase in cephalosporin C bioconversion with use of a Micro pO2 Probe." Biotechnology Techniques, vol. 9, No. 12 (Dec. 1995), pp. 836–868.

Faotto, L. et al. "Amino acid sequence of D–Amino acid oxidase from the yeast *Rhodotorula gracilis*." Flavins and Flavoproteins, 1993 Walter de Gruyter & Co., 1994, Berlin, pp. 163–166.

Faotto, L. et al. "The primary structure of D–amino acid oxidase from *Rhodotorula gracilis*." Biotechnology Letters, vol. 17, No. 2 (Feb. 1995), pp. 193–198.

Pilone Simonetta, M. et al. "Properties of D–amino acid oxidase from *Rhodotorula gracilis*." Eur. J. Biochem., vol. 180, (1989), pp. 199–204.

Fukui, K. et al. "Molecular Cloning and Sequence Analysis of cDNAs encoding porcine kidney d–Amino Acid Oxidase." Biochemistry, vol. 26 (1987), pp. 3612–3618.

* cited by examiner

Primary Examiner—Nashaat T. Nashed
(74) Attorney, Agent, or Firm—Ladas and Parry

(57) ABSTRACT

Process for producing the enzyme D-amino acid oxydase of *Rhodotorula gracilis* in host cells. The process for the expression of the enzyme comprises isolating the complementary DNA corresponding to the messager RNA of the gene which codes for the D-amino acid oxydase of any strain of *Rhodotorula gracillis* producing said enzyme; fusing the fragment of DNA which codes for D-amino acid oxydase of *Rhodotorula gracillis* with a DNA sequence which contains a site of union to the ribosome and a high efficiency promoter sequence for the express of genes in host cells; inserting the DNA fragment into a plasmid appropriate for the host cell; cultivating the host cells transformed with said plasmid; and collecting the enzyme.

12 Claims, No Drawings

PROCESS FOR PRODUCING THE ENZYME D-AMINO ACID OXIDASE OF *RHODOTORULA GRACILIS* IN HOST CELLS

SCOPE OF THE INVENTION

The present invention relates to a process for producing the D-amino acid oxidase enzymatic activity of *Rhodotorula gracilis* in *Escherichia coli*. More particularly, it describes a method for isolating the gene which codes for an enzyme with D-amino acid oxidase activity by the use of recombinant DNA techniques, the cloning of the said gene in a micro-organism of the genus Escherichia, the hyperproduction of the said enzyme by fermentation in the said micro-organism and the extraction of the enzyme. This enzyme can be used for the preparation of 7β-(4-carboxybutanamide) cephalosporanic acid. This acid is an intermediate for the preparation of 7-amino cephalosporanic acid, which in turn is a known intermediate for the preparation of a wide range of antibacterial agents of the cephalosporin family.

STATE OF THE ART

For the production of 7β-(4-carboxybutanamide) cephalosporanic acid, also called glutaryl-7-aminocephalosporanic acid (hereinafter referred to as GL-7ACA), from cephalosporin C, the use of the enzyme D-amino acid oxidase (hereinafter referred to as DAO) originating from different micro-organisms, such as Trigonopsis variabilis (Biochem. Biophys. Res. Commun. (1993) 31:709), *Rhodotorula gracilis* (J. Biol. Chem. (1994) 269:17809) and *Fusarium solani* (J. Biochem. (1990) 108:1063), is known. The production of DAO by the use of these micro-organisms has many disadvantages. Firstly the DAO activity level is very low, and secondly other enzymes such as esterases and catalases are produced apart from the DAO activity. The first of these break down the acid GL-7ACA, thus reducing the yield from the process. The second destroy the hydrogen peroxide needed in catalysis and make it necessary to add this compound—which causes a loss of enzyme activity, reducing the possibilities of re-use. In order to avoid this enzyme contamination it is necessary to purify the DAO—which greatly complicates the enzymatic process for obtaining GL-7ACA from cephalosporin C.

A process for isolating the gene which codes for the DAO of *T. variabilis* and expressing it in *Escherichia coli* and in *T. variabilis* has recently been described (published Japanese Patent Application No. 71180/1988; European Patent Application No. 93202219.7, published as No. 0583817-A2). In addition, the gene which codes for the DAO of *F. solani* has also been cloned and expressed in *Escherichia coli* and *Achremonium chrysogenum* (published Japanese Patent Application No. 2000181/1990; J. Biochem. (1990) 108:1063; Bio-Technology (1991) 9:188).

In addition, it was known that the yeast *Rhodotorula gracilis* expresses DAO (Biotechnol. Appl. Biochem. (1992) 16:252) [lacuna] The advantages offered by the DAO of *Rhodotorula gracilis* is that it has high catalytic efficiency (J. Biol. Chem. (1993) 268:13850) and a low dissociation constant of the FAD which it uses as cofactor (Eur. J. Biochem. (1991) 197:513). The amino acid sequence of the amino-terminal ends of two peptides of this DAO was also known (J. Biol. Chem. (1994) 269:17809), one of them containing an arginine residue involved in the catalysis. More recently its complete amino acid sequence has been published (Biotech. Letters (1965) 17:193). The levels of DAO production by the wild strain *Rhodotorula gracilis* are too low for an industrial process to be developed, however. In the state of the art no process has been found for isolating the gene which codes for the DAO of *Rhodotorula gracilis* and trying to express it either in *Escherichia coli* or in another micro-organism.

DETAILED DESCRIPTION OF THE INVENTION

The starting point for the description of this invention is the yeast *Rhodotorula gracilis* ATCC 26217 as the donor of deoxyribonucleic acid (hereinafter referred to as DNA) and ribonucleic acid (hereinafter referred to as RNA). Once the genomic DNA of the yeast (which contains the gene with the genetic information relating to the production of DAO, also hereinafter called dao gene) had been obtained, it was used as the template for an amplification process known as polymerase chain reaction (hereinafter referred to as PCR), in which two synthetic oligonucleotides which had been designed on the basis of two short amino acid sequences known from the DAO of *Rhodotorula gracilis* were used as primers. The DNA fragment obtained as a product of the PCR amplification process was isolated and introduced into a plasmid vector obtained from a strain of *Escherichia coli*. The recombinant vector was used to obtain the sequence of the DNA fragment which contained part of the dao gene of *Rhodotorula gracilis*.

The genomic DNA of *Rhodotorula gracilis* was then partially digested with the restriction endonuclease Sau3A, and a DNA library was constructed with the resultant DNA fragments, using the phage vector lambda-GEM12 of *Escherichia coli*. The DNA fragment previously cloned by PCR was used as a probe to screen the DNA library, with the aim of isolating the recombinant phages which contained the dao gene. Using the isolated phages which contained the dao gene, the said gene was subcloned in plasmid vectors from *Escherichia coli*. The recombinant vectors thus obtained were used to determine the complete sequence of the dao gene, which turned out to be made up of multiple exons and introns.

As the previously obtained DNA fragment which contains the genomic sequence of the dao gene of *Rhodotorula gracilis* has numerous introns, it cannot be used for its direct expression in *Escherichia coli*. For this reason total RNA of *Rhodotorula gracilis* was isolated and used as a template to obtain complementary DNA (hereinafter referred to as cDNA), using a reverse transcriptase and, as primer, a synthetic oligonucleotide designed on the basis of the nucleotide sequence of the 3' end of the last exon of the dao gene. Once the DNA strand complementary to the RNA corresponding to the dao gene had been obtained, this was used as a template for its amplification by PCR, using two synthetic oligonucleotides designed on the basis of the nucleotide sequences of the 5' and 3' ends corresponding to the first and last exon of the dao gene, respectively. The *Escherichia coli* ribosome binding sequences (hereinafter referred to as RBS), a chain initiation codon and a chain termination codon were included in these synthetic oligonucleotides, as well as various restriction sites useful for the cloning of DNA fragments. A new DNA fragment which, once isolated, was cloned in a plasmid vector from *Escherichia coli* was thus obtained. The recombinant vector was used to determine the sequence of the DNA fragment which represents the messenger RNA of the dao gene of *Rhodotorula gracilis*.

Using the restriction targets created by cloning, the DNA fragment which contained the complete cDNA of the DAO gene of *Rhodotorula gracilis* was subsequently cloned in a plasmid vector from *Escherichia coli* which has a promotor allowing the expression of genes in this host bacterium. In this way a recombinant clone of *Escherichia coli* was obtained which produced an active DAO, and which was deposited in the Spanish Collection of Type Cultures (CECT), Department of Microbiology, Faculty of Biological Sciences, University of Valencia, 46100 Burjasot (valencia), as No. 4636.

In order to produce DAO, using the previously selected recombinant clone of *Escherichia coli*, it is grown in a medium containing a carbon source, a nitrogen source and mineral salts. The temperature for this production process is between 18 and 30° C., and the pH must be kept between 5 and 9. Flasks of different volumes, from 50 ml to 1000 ml, with a quantity of medium between 10 and 50% of the volume of the flask, can be used for flask fermentation. One fermentation lasts for a period of between 12 and 90 hours.

The cultivation of the recombinant micro-organisms can be improved if suitable conditions for maintaining the stability of the recombinant vectors are chosen—which is achieved by adding antibiotics to the culture medium, such as chloramphenicol, kanamycin or tetracycline, for which the recombinant vector containing the dao gene presents a resistance marker. In addition to stability of production, this prevents the culture medium being contaminated with other unwanted micro-organisms and also eliminates the strains which, because they have lost the recombinant vector, have ceased to produce DAO.

The DAO produced by the recombinant clones can be extracted by separating the cells from the culture medium by centrifugation and subsequent disruption or permeabilization of the cells by chemical, enzymatic or mechanical processs. If an enzyme extract of greater purity is needed, the DAO can be purified by conventional precipitation, filtration or chromatographic, etc. techniques.

Using the DAO obtained from the recombinant clones of *Escherichia coli* which expressed the dao gene of *Rhodotorula gracilis*, it is possible to produce GL-7ACA from cephalosporin C. The concentrated enzyme extracts can also be immobilized by making them react with suitable inert solid supports, and in this way the immobilized DAO can be used cyclically.

The novelty of this invention resides in the fact that it is the first time that the enzyme DAO of the yeast *Rhodotorula gracilis* can be expressed in a prokaryotic micro-organism such as *Escherichia coli*. In this way it is possible to obtain an increase in production which would facilitate the use of this enzyme on an industrial scale. The possibility of producing the enzyme in various *Escherichia coli* strains which lack unwanted enzymes such as catalase or esterases, and also the possibility of improving the stability thereof and facilitating the purification thereof by modifying it by protein engineering techniques, are other aspects which increase the novelty concept of this patent.

The present invention will be illustrated in greater detail in the Examples which follow.

EXAMPLE 1

1. DAO Activity Assay

The assay was performed by the previously-described process (J. Biol. Chem. (1967) 242:3957), using D-phenylglycine (25 mM) as substrate. The incubation is carried out in 50 mM phosphate buffer, pH 8.0, containing 5 µM FAD, for 15 to 30 minutes. The reaction is stopped with 1/10 by volume pure acetic acid. The variation in the O.D. at 252 nm determines the activity of the enzyme, taking into account that 89.2 nmol of the benzoylformic acid which arises in the reaction exhibits an $O.D._{252}$ of 1.0. One unit (U) is equivalent to 1 nmol of substrate transformed per minute.

2. Preparation of the Vector DNAs and of the Competent *Escherichia coli* Cells for the Transformation The plasmid vector pBCKS/+(Cm$^r$) (Stratagene), which contains a resistance marker for chloramphenicol, was prepared as follows: The *Escherichia coli* strains individually possessing the aforesaid plasmid were incubated for 16 hours with shaking in an orbital shaker at 250 rpm and at 37° C. in 0.5 litres of LB medium containing 10 g/l of yeast extract and 5 g/l of NaCl. After the time indicated had elapsed, the cells were sedimented, washed and lysed, and the plasmids were isolated by the alkaline method (Sambrook et al. (1989) Molecular Cloning: A laboratory manual, Cold Spring Harbor Laboratory, Cold Spring Harbor, N.Y., USA). The plasmid DNA obtained by this method was purified by centrifugation in CsCl gradient.

The competent *Escherichia coli* cells were obtained by the RbCl process (Sambrook et al. (1989) Molecular Cloning: A laboratory manual, Cold Spring Harbor Laboratory, Cold Spring Harbor, N.Y., USA). In essence the strains *Escherichia coli* DH5α (Sambrook et al. (1989) Molecular Cloning: A laboratory manual, Cold Spring Harbor Laboratory, Cold Spring Harbor, N.Y., USA) and *Escherichia coli* DH10B (Life Technologies, Gaithersburg, Md.) were used for the cloning and analysis of fragments.

3. Preparation of the Donor DNA which has the Genetic Information Relating to the Production of DAO The strain of *Rhodotorula gracilis* ATCC 26217 was grown in a YMPG medium containing: malt extract (0.3%), yeast extract (0.3%), peptone (0.5%) and glucose (1%). Incubation was carried out for 36 hours until an $O.D._{660}$ of 5.0 was attained, with shaking in an orbital shaker at 250 rpm and at a temperature of 30° C.

The cells were then sedimented, washed and lysed with zymolyase, and the DNA was extracted by a previously-described process (Sherman et al. (1986) Laboratory Course for Methods in Yeast Genetics, Cold Spring Harbor Laboratory, Cold Spring Harbor, N.Y.). In order to achieve greater purity, the DNA was treated with RNAse and then extracted repeatedly with phenol and chloroform-isoamyl alcohol, and the DNA was precipitated in the aqueous phase with isopropanol. The precipitated DNA was washed with 100% ethanol and 70% ethanol and dissolved in a 10 mM Tris-HCl buffer, pH 7.5, containing 1 mM EDTA (TE buffer).

4. Use of PCR to Obtain a DNA fragment Containing the dao gene of *Rhodotorula gracilis*

An 0.15-µg sample of the DNA of *Rhodotorula gracilis* was mixed with 0.01 µl (25 µM) of each of the degenerate oligonucleotides RG1 (SEQ ID NO:2) (5'GACT(C/G)CC(C/G)GAGGACGT(C/T/G)(T/A)(C/G)(T/A)(C/G)(G/C)CAGAC-3') and RG2 (SEQ ID NO:3) (5'-GC(C/G)GG(G/C/T)CG(A/C/G)AG(G/A/C)CC(G/A/C)ACGTTGTG-3') which code for the amino acid sequences DLPEDVSSQT (SEQ ID NO:6) and HNVGLRPA (SEQ ID NO:7), respectively. To this mixture were added 2.5 units of Taq polymerase (Perkin-Elmer) together with the appropriate buffer recommended by the suppliers, and the preparation was subjected to an amplification process in a PCR unit (GeneATAQ, Pharmacia) using 30 cycles, each cycle being 98° C. (1 minute), 55EC (2 minutes) and 72EC (2.5 minutes). The result of the amplification was visualized by dyeing with ethidium bromide after 1% agarose gel electrophoresis.

The DNA fragment obtained by PCR, of a size of approximately 1 kb, was purified by extraction of the agarose gel using $-agarase (Biolabs), in accordance with the suppliers' recommendations.

5. Cloning and Sequencing of the Fragment Obtained by PCR which Contains the dao gene An 0.1-Fg sample of DNA of the plasmid pBCKS/+ was digested with the restriction endonuclease EcoRV (Pharmacia) at 37° C., in a buffer recommended by the suppliers, for 1 hour, and was heated for 10 minutes at 65° C. in order to stop the reaction. The digested plasmid was mixed with a sample of the previously-purified DNA fragment resulting from the PCR (0.2 Fg), and both DNAs were ligated by means of the enzyme T4 DNA ligase (Amersham), in the presence of ATP, using a buffer recommended by the suppliers.

The resultant ligation mixture was used to transform competent *Escherichia coli* DH5" cells. The transformants were isolated in a solid culture medium with agar (2%) which contained LB medium, chloramphenicol (34 Fg/ml), X-gal (40 Fg/ml) and 0.2 mM IPTG. By this process various clones were obtained which presented a white phenotype in the selection medium. One of these clones contained the recombinant plasmid pPCR20 which possesses the 1-kb DNA fragment resulting from the amplification by PCR, inserted at the EcoRV site of the plasmid pBCKS/+.

The nucleotide sequence of the fragment contained in the plasmid pPCR20 was determined on the same plasmid by a method described earlier (Sanger et al. (1977) Proc. Natl. Aca. Sci. USA 74:5463–5464), using the T7 DNA Polymerase Kit (Pharmacia), [$^{35}$S]dCTP as radioactive marker and commercial or synthetic oligonucleotides as primers. The nucleotide sequence revealed that the cloned fragment had 0.995 kb. Analyses of the sequence and comparison thereof with other known sequences in international databases (GeneBank/EMBL) indicated that the cloned fragment coded for part of the dao gene of *Rhodotorula gracilis*.

EXAMPLE 2

1. Construction of a *Rhodotorula gracilis* DNA library

The total DNA of the strain *Rhodotorula gracilis* ATCC 2617 was obtained as described in Section 3 of Example 1. A total of 300 Fg of the said total DNA was partially digested with 20 units of Sau3A1 in a reaction volume of 600 Fl at 37° C. and 3 aliquots of 200 Fl were collected at 45 seconds, 1 minute and 2 minutes, respectively, digestion being stopped with cold 20 mM EDTA. After checking the digests in an 0.7% agarose gel, they were mixed, heated at 68° C. for 10 minutes, left to cool slowly to ambient temperature and placed on a 38-ml sucrose gradient (10–40%). This gradient was centrifuged at 26,000 rpm for 24 hours at 15° C., aliquots of 0.5 ml being collected, 10 Fl of which was analyzed in an 0.4% agarose gel. The aliquots whose DNA had a size between 18 and 22 kb were mixed and diluted with distilled water to approximately 10% sucrose. The DNA was then precipitated with ethanol and resuspended in 50 Fl of a TE buffer, and 3 Fl of this last solution was analysed in an 0.4% agarose gel. In this gel it was verified that the size of the DNA fragments was correct and that the concentration thereof was approximately 50 ng/Fl.

The DNA of the bacteriophage lambda-GEM12 (Promega) was prepared in parallel, essentially as described earlier (Sambrook et al. (1989) Molecular Cloning: A laboratory manual, Cold Spring Harbor Laboratory, Cold Spring Harbor, N.Y., USA). For this purpose, the strain *Escherichia coli* LE392 (Sambrook et al. (1989) Molecular Cloning: A laboratory manual, Cold Spring Harbor Laboratory, Cold Spring Harbor, N.Y., USA) was grown for 10 hours in NZCYM-0.2% maltose (Sambrook et al. (1989) Molecular Cloning: A laboratory manual, Cold Spring Harbor Laboratory, Cold Spring Harbor, N.Y., USA) and its O.D. was measured at 600 nm. The volume of culture corresponding to 3×10$^9$ cells was centrifuged at 4,000 rpm for 10 minutes at 4° C. in a table centrifuge and resuspended in 1.2 ml of 50 mM Tris-HCl buffer, pH 7.5, containing 0.1 M NaCl, 2 g/l MgSO$_4$0.7 and 0.01% gelatin (SM buffer). 3×10$^7$ plaque-forming units (pfu) of the phage lambda-GEM12 were added to these cells, and the mixture was incubated for 30 minutes at 37° C. without shaking. Each of the flasks (of 500 ml, with 100 ml of NZCYM-0.2% maltose medium) pre-heated to 37° C. was inoculated with 200 Fl of the infected cells. The said flasks were incubated at 37° C. until the culture appeared lysed (5–6 hours). The lysates were treated with DNase (1 Fg/ml) and RNase (2 Fg/ml) for 45 minutes at ambient temperature. 5.8 grammes of NaCl was then added for each 100 ml of lysate and the mixture was kept for 60 minutes on ice. After this time had elapsed, it was filtered to eliminate the cellular residues. After adding 20 ml of 50% PEG-6,000 for every 100 ml of lysate, the mixture was kept for 60 minutes on ice and centrifuged at 10,000×g for 20 minutes at 4° C. The precipitate was resuspended in 1 ml of TM and extracted twice with a mixture of chloroform and isoamyl alcohol (24/1) (CIA) in order to eliminate the PEG-6000 residues without disrupting the phage. It was subsequently extracted twice with neutral phenol, once with phenol-CIA and once with CIA. The aqueous phase was brought to 0.5 M NaCl (with 4 M NaCl) and the DNA was precipitated with two volumes of ethanol at −20° C. After it had been centrifuged for 20 minutes at 4° C. in a mini-centrifuge, the DNA precipitated was washed with 70% ethanol, dried and resuspended in 50 Fl of TE.

50 Fg of DNA from the bacteriophage was digested with the endonucleases BamHI and XbaI at 37° C. for 2 hours. The double digest was extracted with phenol-CIA and CIA, precipitated with ethanol and resuspended in 50 Fl of TE. After collection of an aliquot of 2 Fl, MgCl$_2$ was added to the remainder up to 10 mM and it was incubated at 42° C. for 1 hour in order to encourage the recirculization of the arms of the vector by its cohesive ends. A 2-Fl fraction which was analysed together with the previous one in an 0.5% agarose gel was again collected. After correct recircularization by the cohesive ends had been verified, the mixture was placed on a 38-ml sucrose gradient (10–40%). In this case the DNA was not heated at 68° C. before it was placed on the gradient, as this would lead to separation of the cohesive ends of the phage. The gradient was centrifuged at 26,000 rpm for 24 hours at 15° C., subsequently being collected in aliquots of 0.5 ml. After analyzing 15 Fl of each of these in an 0.5% agarose gel, those which lacked the dispensable central fragment or "stuffer" were mixed and diluted with distilled water up to about 10% sucrose. The DNA was precipitated with ethanol and resuspended in 50 Fl of TE, and 2 Fl of this last solution was visualized in an agarose gel (0.5%) in order to confirm the absence of the central fragment and estimate that its approximate concentration was 100 ng/Fl.

A series of ligations were then performed, using 0.25 Fg of insert and quantities of vector ranging from 0.25 to 0.75 Fg, varying the insert/vector ratio. The reactions were incubated at 12–14° C. for 16 hours. After verifying, in an 0.4% agarose gel, that DNA fragments (produced by ligation) of greater size than that of the vector or insert had appeared, all the ligation reactions were mixed, precipitated with ethanol and resuspended in 4 Fl of ligation buffer.

The encapsidation of the recombinant phage DNA produced after the ligation was carried out with Packagene (Promega) "in vitro" packaging extracts. The result of the encapsidation reaction, resuspended in 500 Fl of SM, was used to make infections of *Escherichia coli* LE392 in order to titrate the number of phages present and the number of *Escherichia coli* NM539 (Promega), with the aim of determining the percentage of recombinant phages. *Escherichia coli* NM539 is a lysogenic strain of the phage P2 and only produces lysis plaques when the phage which infects it lacks the dispensable central region. The phage titre was found to be 132 pfu/Fl (a total of 66,000 pfu) in *Escherichia coli* LE392 and 113 pfu/Fl in *Escherichia coli* NM539. This meant that about 85% of the phages were carrying an exogenous DNA fragment. In order to calculate the number of recombinant phages needed to make up a complete genetic library, Clarke & Carbon's equation was applied, $N=\ln(1-p)/\ln(1-f)$, where p is the desired probability, f is the proportion of the genome of the selected organism which is contained in a recombinant, and N is the number of recombinants needed. Assuming that the size of the genome of *Rhodotorula gracilis* is contained in about 15,000 kb and that the average of the encapsidated inserts was 18 kb (in spite of the fact that sizes between 18 and 22 kb had been selected), a *Rhodotorula gracilis* DNA library had been produced with 99.99% probability with the number of recombinant phages obtained.

After this series of theoretical verifications had been carried out, *Escherichia coli* NM539 was infected and the complete genetic library was spread on 5 Petri dishes of 150 mm diameter (about 11,300 pfu/Petri dish), subsequently being collected in 50 ml of SM. Of this 50 ml, 40 ml was taken and 2.5 ml of chloroform was added to it before storing it at 4° C. 7% DMSO was added to the remaining 10 ml and it was stored at −80° C. In this way a solution was obtained which contained a number of recombinant phages amounting to approximately 5,300 pfu/Fl prepared for analysis.

2. Identification of the Clones which Contain the dao gene

Approximately 60,000 pfu were spread on 2 Petri dishes of 150 mm diameter (about 30,000 pfu/Petri dish) and transferred with a nitrocellulose filter. Assuming an average insert of 18 kb for every pfu and 15,000 kb for the genome of *Rhodotorula gracilis*, the said genome would be represented about 72 times. In this case the bacterium selected for infection was *Escherichia coli* LE392, as the number of false recombinants was negligible and the size of the lysis plaques was greater and more uniform than obtained with *Escherichia coli* NM539.

The process of selecting positive phages was carried out in accordance with a hybridization process described earlier (Sambrook et al. (1989) Molecular Cloning: A laboratory manual, Cold Spring Harbor Laboratory, Cold Spring Harbor, N.Y., USA). The process commenced with the prehybridization of the nitrocellulose filters. For this purpose the filters were incubated at 42° C. for 3 hours in hybridization buffer (Sambrook et al. (1989) Molecular Cloning: A laboratory manual, Cold Spring Harbor Laboratory, Cold Spring Harbor, N.Y., USA). The hybridization was carried out by removing the buffer used in the pre-hybridization and introducing a new hybridization buffer together with 200 ng of the DNA fragment labelled with previously-denatured $^{32}$p. The DNA which was used as a probe for identification of the clones carrying the dao gene consisted of a fragment of 900 pb obtained by EcoRI-HindIII digestion of pPCR20. The filters were incubated at 42° C. for 16 hours and washed twice for 20 minutes at ambient temperature in 2×SSC-0.1% SDS, followed by a further two washings for the same length of time at the hybridization temperature in 0.1×SSC-0.1% SDS buffer (Sambrook et al. (1989) Molecular Cloning: A laboratory manual, Cold Spring Harbor Laboratory, Cold Spring Harbor, N.Y., USA). Finally, the nitrocellulose filters were exposed in Hyperfilm-MP (Amersham) under amplification screens at 70° C. for 48 hours.

Once the process of pre-hybridization, hybridization, washings and autoradiography was completed, a total of 16 positive clones were selected from the 54 obtained. The positive lysis plaques were collected individually with the aid of a Pasteur pipette and each of them was resuspended in 1 ml of SM plus 50 Fl of chloroform. The phages present in this solution were then titrated. For this purpose it was necessary to dilute the said phage 5,000 times in order to ensure that when infection was carried out with 20 Fl of it, the number of lysis plaques per Petri dish would be between 500 and 1,000. Once the contents of each Petri dish had been transferred to the corresponding nitrocellulose filter, the latter were hybridized again with the same probe. Autoradiography showed that between 20 and 50% of the phages from each Petri dish generated a positive signal. It was therefore necessary to purify each of the positive phages by means of a third hybridization cycle. For this purpose, a Pasteur pipette was used to collect those positive lysis plaques which were more isolated from the rest or which were surrounded by lysis plaques that were also positive, and they were resuspended in 1 ml of SM plus 50 Fl of chloroform. After diluting this phage solution 100 times and infecting with 15 Fl thereof, titres of about 300 lysis plaques per Petri dish were achieved. After processing under identical conditions to the two previous cycles, the result was achieved that 100% of the phages from each Petri dish were positive. In this way 16 independent lysis plaques were purified. Each lysis plaque was resuspended in 100 Fl of SM plus 10 Fl of chloroform, and with 2 Fl of this solution confluent lysis plaques were obtained with the aim of amplifying the said positive phages on a solid medium. After collecting the top layer of agarose and resuspending it in 5 ml of SM, solutions with about 107 pfu/Fl were obtained for each of the positive phages.

Using Southern's method (Sambrook et al. (1989) Molecular Cloning: A laboratory manual, Cold Spring Harbor Laboratory, Cold Spring Harbor, N.Y., USA), the above-mentioned 900 pb EcoRI-HindIII probe was also used to determine those genomic DNA fragments which included the dao gene of *Rhodotorula gracilis*. For this purpose, hybridization with the DNA digested with the restriction endonucleases (Pharmacia) BamHI, EcoRI, HindIII, KnpI, PstI, PvuII, XbaI and XHOI and fractionated in agarose gel was carried out under the conditions described below. The agarose gel in which DNA fragments were separated on the basis of their molecular size was sequentially incubated at ambient temperature and with gentle shaking for 15 minutes in 0.25 M HCl, for 1 hour in denaturing solution and 1 hour in neutralizing solution. The gel was then placed on a wad of Whatman 3MM filter papers soaked in 10×SSC, and a BA85 nitrocellulose filter (0.45 Fm) (Schleicher and Schuell) of the same dimensions as the gel was placed on it and soaked in 2×SSC, taking care to avoid the formation of bubbles. Two sheets of Whatman 3MM paper soaked in 2×SSC were placed on the nitrocellulose filter, and 8–10 centimetres in height of dry filter-paper of the same dimensions were placed on top, and on top of all this a weight of about 500 grammes. The transference was maintained for 16 hours. Once the DNA had been transferred, the nitrocellulose filter was carefully submerged in 6×SSC for 5 minutes, left to dry for 1 hour at ambient temperature and incubated between two sheets of Whatman 3MM paper at 80° C. with vacuum for 3 hours plus. It was then pre-hybridized and hybridized under the same conditions as described earlier for the screening of the DNA library. The result of the autoradiography showed the appearance of specific hybridization bands for each of the digests. To be precise, the size of these bands was 8.4 kb for the EcoRI digest and 3.5 kb for the HindIII. After purifying the DNA of the phages as indicated in Section 1 of Example 2 for the bacteriophage lambda-GEM12, EcoRI and HindIII digestions were performed, the above-mentioned 8.4 kb EcoRI and 3.5 HindIII bands being identified. Southern's method confirmed that both bands hybridize specifically with the 900pb EcoRI-HindIII probe from pPCR20.

With the aim of subcloning the above-mentioned 8.4 kb EcoRI and 3.5 kb HindIII fragments, 5 Fg of phage #11 was digested with EcoRI and a further 5 Fg with HindIII, and the desired fragments were purified by the GENECLEAN II method (BIO 101, Inc.) and ligated with the plasmid pBCKS/+ (Stratagene) digested with EcoRI or HindIII, using T4 DNA ligase, ATP and the buffer recommended by the enzyme suppliers. The resultant ligation mixture was incubated for 5 hours at 12° C. and used to transform competent *Escherichia coli* DH5" cells. The transformants were selected in a solid LB medium to which chloramphenicol (34 Fg/Fl), X-gal (40 Fg/Fl) and 0.2 mM IPTG had been added. Among the clones which presented the white selection phenotype, those which carried the 3.5-kb HindIII fragment (both orientations) were identified as pALR90 and pALR91, and those which included the 8.4-kb EcoRI fragment (both orientations) were identified as pALR92 and pALR93.

3. Sequencing of the Fragment Containing the dao gene

The DNA fragment which is contained in the plasmid pARL90 and which codes for the dao gene of *Rhodotorula gracilis* was sequenced using the same process as described for the sequencing of the insert of the plasmid pPCR20, in this case using synthetic oligonucleotides as primers designed on the basis of the sequence determined previously with the plasmid pPCR20. This sequence is shown in SEQ ID NO:1.

EXAMPLE 3

1. Extraction of the Total RNA of *Rhodotorula gracilis*

The strain *Rhodotorula gracilis* ATCC 26217 was grown in the YMPG medium described earlier. Incubation lasted 15 hours (O.D.$_{660}$=1.13) with shaking in an orbital shaker at 250 rpm and at a temperature of 30° C.

The RNA was extracted by a process described earlier (Methods Enzymol. (1991) 194:398) using hot phenol and glass beads.

2. Obtaining the cDNA Corresponding to the dao gene

A sample of 7 Fg of total RNA from *Rhodotorula gracilis* containing RNAsine was circularized at 70EC for 5 minutes with 2 Fl of the oligonucleotide RTDA02 SEQ ID NO:4 (5'-CCATCGATAAGCTTACAACTTCGACTCCCGCGCC GC-3') (10 FM). The resultant product was incubated at 42° C. for 90 minutes with the reverse transcriptase AMV (Promega), using the buffer and conditions indicated by the suppliers. The mixture was then heated at 95° C. for 5 minutes and diluted 4 times with distilled water.

The resultant product was used as a template for amplification by PCR. For this purpose use was made of the oligonucleotides RTDA01 SEQ ID NO:5 (5'-GGAGGAATTCATATGCACTCTCAGAAGCGCGTCG-3') and RTDA02, described above. The oligonucleotide RTDA01 brings the nucleotide sequence GGAGG which represents a binding site to the *Escherichia coli* ribosome which will be needed for the production of DAO in this micro-organism. The amplification process was similar to that described earlier, but in this case using 30 cycles of 95° C. (1 minute), 55° C. (2 minutes) and 72° C. (2 minutes). The result of the amplification was visualized by dyeing with ethidium bromide after 1% agarose gel electrophoresis.

The DNA fragment obtained by PCR, approximately 1.1 kb in size, was purified by extraction of the agarose gel using Geneclean (Bio 101, Inc.), in accordance with the suppliers' recommendations.

3. Cloning and sequencing of the DNA Fragment Corresponding to the Messenger RNA of the dao gene An 0.1-Fg sample of DNA of the plasmid pBCKS/+ was digested with the restriction endonuclease EcoRV (Pharmacia) at 37° C., in a buffer recommended by the suppliers, for 1 hour, and was heated for 10 minutes at 65° C. in order to stop the reaction. The digested plasmid was mixed with a sample of the previously-purified DNA fragment resulting from the PCR (0.2 Fg), and both DNAs were ligated by means of the enzyme T4 DNA ligase (Amersham), in the presence of ATP, using a buffer recommended by the suppliers.

The resultant ligation mixture was used to transform competent *Escherichia coli* DH5" cells. The transformants were isolated in a solid culture medium with agar (2%) which contained LB medium, chloramphenicol (34 Fg/ml), X-gal (40 Fg/ml) and 0.2 mM IPTG. By this process various clones were obtained which presented a white phenotype in the selection medium. One of these clones contained the recombinant plasmid pCDAAO10 which possesses the 1.1-kb DNA fragment resulting from the amplification by PCR, inserted at the EcoRV site of the plasmid psCKS/+. This clone was deposited in the Spanish Collection of Type Cultures (CECT) as No. 4636.

The nucleotide sequence of the fragment contained in the plasmid pCDAA03 was determined by the same method as described earlier. The nucleotide sequence and comparison thereof with other known sequences in international databases (GeneBank/EMBL), and also with the recently-published amino acid sequence of the DAO of *Rhodotorula gracilis* (Biotech. Letters (1995) 17:193), indicated that the cloned fragment contained the region of the cDNA which codes for the DAO of *Rhodotorula gracilis*. The exons corresponding to the cDNA which code for the DAO of *Rhodotorula gracilis* are indicated in SEQ ID NO: 1. This analysis also showed that the fragment cloned in the plasmid pCDAAO10 contains the dao gene in the right orientation for its expression under the control of the lac promoter of the vector, and so this plasmid allows DAO to be produced under the control of this promoter.

EXAMPLE 4

1. Production of the DAO of *Rhodotorula gracilis* in *Escherichia coli*

The strain *Escherichia coli* CECT 4636 was fermented in LB medium for 20 hours at 25° C., with shaking at 250 rpm. The cells were then collected by centrifugation at 5,000×g for 10 minutes and disrupted by sonication, and their DAO activity was assayed as described in Section 1 of Example 1. The DAO activity obtained by this process was 40 U/mg of protein.

What is claimed is:

1. A process comprising producing a *Rhodotorula gracilis* D-amino acid oxidase enzyme by the steps of:
   (a) transforming a prokaryotic host cell with a recombinant DNA molecule comprising
      (i) a DNA sequence encoding said enzyme, wherein said DNA sequence comprises SEQ ID NO:8;
      (ii) a ribosome binding site and
      (iii) a promoter operatively coupled to said DNA sequence to direct expression of the enzyme in said host cell, wherein the prokaryotic host cell is capable of stable production of said enzyme and is devoid of any other enzyme that would degrade glutaryl-7-aminocephalosporanic acid or hydrogen peroxide;
   (b) growing the transformed host cell in a culture medium under conditions that cause the host cell to produce said enzyme; and
   (c) recovering the enzyme from the culture medium.

2. A process according to claim 1, wherein the DNA sequence encoding said enzyme is a c-DNA formed from an m-RNA molecule naturally occurring in a strain of *Rhodotorula gracilis*.

3. A process according to claim 2, wherein said transforming step comprises
   (i) inserting said recombinant DNA molecule into a plasmid vector that replicates in the host cell and
   (ii) transforming the host cell with said plasmid vector.

4. A process according to claim 1, wherein said recovering step (c) consists essentially of centrifugation and subsequent disruption of the host cell without further purification of the enzyme.

5. A process according to claim 1, wherein the host cell grown in step (b) produces at least 40 U/mg of the enzyme.

6. A process according to claim 1, wherein the transformed host cell is grown in step (b) in LB medium for at least 20 hours at 25° C.

7. A process according to claim 1, wherein the host cell is *Escherichia coli*.

8. A process according to claim 1, wherein the host cell is a pure strain of *Escherichia coli* CECT 4636.

9. An isolated DNA molecule encoding the amino acid sequence of SEQ ID NO:9, said DNA molecule comprising SEQ ID NO:8.

10. A vector comprising the DNA molecule of claim 9.

11. A prokaryotic host cell comprising the DNA molecule of claim 9 and expressing D-amino acid oxidase.

12. A host cell according to claim 11 which is a strain of *Escherichia coli* CECT 4636.

* * * * *

SEQUENCE LISTING

<160> NUMBER OF SEQ ID NOS: 9

<210> SEQ ID NO 1
<211> LENGTH: 1541
<212> TYPE: DNA
<213> ORGANISM: Rhodotorula gracilis

<400> SEQUENCE: 1

```
aacgaggggt gtcgctcgac taacagctct ctatcctctt gctgctagca          50
ttgtactact cgaacgacgc c atg cac tct cag aag cgc gtc gtt         95
                        Met His Ser Gln Lys Arg Val Val
                         1               5 gtc ctc gga tca ggc ggt gcgtcttttc cctctcctcc ccacacccga       143
Val Leu Gly Ser Gly Gly
         10
cagtcctcga cgaggtgtag dacggcgagc aaagctgccg agggcgatct         193
gggctgactg agcgctcgag tgtaca gtt atc ggt ctg agc agc            237
                             Val Ile Gly Leu Ser Ser
                                      15 gcc ctc atc ctc gct cgg aag ggc tac agc gtg cat att ctc         279
Ala Leu Ile Leu Ala Arg Lys Gly Tyr Ser Val His Ile Leu
 20                  25                  30 gcg cgc gac ttg ccg gag gac gtc tcg agc cag act ttc gct         321
Ala Arg Asp Leu Pro Glu Asp Val Ser Ser Gln Thr Phe Ala
 35                  40                  45 tca cca tgg gct gtgcgtcgtc tcactgtagt tggaggatgt                363
Ser Pro Trp Ala
         50 cagcgagagc tgagcaatct cgtcatcccc gcag ggc gcg aat tgg           409
                                     Gly Ala Asn Trp
                                              55 acg cct ttc atg acg ctt aca gac ggt cct cga caa gca             448
Thr Pro Phe Met Thr Leu Thr Asp Gly Pro Arg Gln Ala
                 60                  65 aaa tgg gaa gaa tcg act ttg tgcgtctcct tctacctcat               489
Lys Trp Glu Glu Ser Thr Phe
 70                  75 tcttggcctc gagctgacga gtgtatgata cacagc aag aag tgg gtc         537
                                       Lys Lys Trp Val gag ttg gtc ccg acg ggc cat gcc atg tgg ctc aag ggg acg         579
Glu Leu Val Pro Thr Gly His Ala Met Trp Leu Lys Gly Thr
 80                  85                  90 agg cgg ttc gcg cag aac gaa gac ggc ttg ctc ggg cac tgg         621
Arg Arg Phe Ala Gln Asn Glu Asp Gly Leu Leu Gly His Trp
         95                 100                 105 tac aag gac atc acg cca aat gtgcgcccac attcactctt               662
Tyr Lys Asp Ile Thr Pro Asn
         110
cccttcgcat gtctccgttt actgacccgc cctctttcgc cgtgcgcag           711 tac cgc ccc ctc cca tct tcc gaa tgt cca cct ggc gct atc         753
Tyr Arg Pro Leu Pro Ser Ser Glu Cys Pro Pro Gly Ala Ile
115                 120                 125 ggc gta acc tac gac acc ctc tcc gtc cac gca cca aag tac         795
Gly Val Thr Tyr Asp Thr Leu Ser Val His Ala Pro Lys Tyr
         130                 135                 140 tgc cag tac ctt gca aga gag ctg cag aag ctc ggc gcg acg         837
Cys Gln Tyr Leu Ala Arg Glu Leu Gln Lys Leu Gly Ala Thr
                 145                 150                 155
```

```
ttt gag aga cgg acc gtt acg tcg ctt gag cag gcg ttc gac              879
Phe Glu Arg Arg Thr Val Thr Ser Leu Glu Gln Ala Phe Asp
            160                 165                 170 ggt gcg gat ttg gtg gtc aac gct acg gga ctt  ggtatgtccc              922
Gly Ala Asp Leu Val Val Asn Ala Thr Gly Leu
                175                 180 gaactgcccc tctctacctg caattttgct gattgatatg  ctcgca ggc              971
                                                    Gly gcc aag tcg att gcg ggc atc gac gac caa gcc gcc gag                 1010
Ala Lys Ser Ile Ala Gly Ile Asp Asp Gln Ala Ala Glu
        185                 190                 195 cca atc cgc ggc caa acc gtc ctc gtc aag tcc cca tgc aag             1052
Pro Ile Arg Gly Gln Thr Val Leu Val Lys Ser Pro Cys Lys
                200                 205 cga tgc acg atg gac tcg tcc gac ccc gct tct ccc gcc tac             1094
Arg Cys Thr Met Asp Ser Ser Asp Pro Ala Ser Pro Ala Tyr
210                 215                 220 atc att ccc cga cca ggt ggg gaa gtc atc tgc ggc ggg acg             1136
Ile Ile Pro Arg Pro Gly Gly Glu Val Ile Cys Gly Gly Thr
    225                 230                 235 tac ggg gtg gga gac tgg gac ttg tct gtc aac cca gag acg             1178
Tyr Gly Val Gly Asp Trp Asp Leu Ser Val Asn Pro Glu Thr
            240                 245                 250 gtc cag cgg atc ctc aag cac tgc ttg cgc ctc gac ccg acc             1220
Val Gln Arg Ile Leu Lys His Cys Leu Arg Leu Asp Pro Thr
                255                 260                 265 atc tcg agc gac gga acg atc gaa ggc atc gag gtc ctc cgc             1262
Ile Ser Ser Asp Gly Thr Ile Glu Gly Ile Glu Val Leu Arg
                    270                 275 cac aac gtc ggc ttg cga cct gca cga cga ggc gga ccc cgc             1304
His Asn Val Gly Leu Arg Pro Ala Arg Arg Gly Gly Pro Arg
280                 285                 290 gtc gag gca gaa cgg atc gtc ctg cct ctc gac cgg aca aag             1346
Val Glu Ala Glu Arg Ile Val Leu Pro Leu Asp Arg Thr Lys
    295                 300                 305 tcg ccc ctc tcg ctc ggc agg ggc agc gca cga gcg gcg aag             1388
Ser Pro Leu Ser Leu Gly Arg Gly Ser Ala Arg Ala Ala Lys
            310                 315                 320 gag aag gag gtc acg ctt gtg cat gcg tat ggc ttc tcg agt             1430
Glu Lys Glu Val Thr Leu Val His Ala Tyr Gly Phe Ser Ser
                325                 330                 335 gcg gga tac cag cag agt tgg ggc gcg gcg gag gat gtc gcg             1472
Ala Gly Tyr Gln Gln Ser Trp Gly Ala Ala Glu Asp Val Ala
                    340                 345 cag ctc gtc gac gag gcg ttc cag cgg tac cac ggc gcg gcg             1514
Gln Leu Val Asp Glu Ala Phe Gln Arg Tyr His Gly Ala Ala
350                 355                 360 cgg gag tcg aag ttg tagggcgggt tt                                   1541
Arg Glu Ser Lys Leu
    365

<210> SEQ ID NO 2
<211> LENGTH: 27
<212> TYPE: DNA
<213> ORGANISM: Artificial Sequence
<220> FEATURE:
<221> NAME/KEY: primer _bind
<223> OTHER INFORMATION: primer for amplifying the dao gene of
      Rhodotorula gracilis

<400> SEQUENCE: 2
```

```
gactsccsga ggacgtbwsw sscagac                                          27
```

```
<210> SEQ ID NO 3
<211> LENGTH: 23
<212> TYPE: DNA
<213> ORGANISM: Artificial Sequence
<220> FEATURE:
<221> NAME/KEY: primer _bind
<223> OTHER INFORMATION: primer for amplifying the dao gene of
      Rhodotorula gracilis

<400> SEQUENCE: 3
gcsggbcgva gvccvacgtt gtg                                              23
```

```
<210> SEQ ID NO 4
<211> LENGTH: 36
<212> TYPE: DNA
<213> ORGANISM: Artificial Sequence
<220> FEATURE:
<221> NAME/KEY: primer _bind
<223> OTHER INFORMATION: primer for amplifying cDNA corresponding to
      the dao gene

<400> SEQUENCE: 4
ccatcgataa gcttacaact tcgactcccg cgccgc                                36
```

```
<210> SEQ ID NO 5
<211> LENGTH: 34
<212> TYPE: DNA
<213> ORGANISM: Artificial Sequence
<220> FEATURE:
<221> NAME/KEY: primer _bind
<223> OTHER INFORMATION: primer for amplifying cDNA corresponding to
      the dao gene

<400> SEQUENCE: 5
ggaggaattc atatgcactc tcagaagcgc gtcg                                  34
```

```
<210> SEQ ID NO 6
<211> LENGTH: 10
<212> TYPE: PRT
<213> ORGANISM: Rhodotorula Gracilis
<220> FEATURE:

<400> SEQUENCE: 6

Asp Leu Pro Glu Asp Val Ser Ser Gln Thr
                5                   10
```

```
<210> SEQ ID NO 7
<211> LENGTH: 8
<212> TYPE: PRT
<213> ORGANISM: Rhodotorula Gracilis

<400> SEQUENCE: 7

His Asn Val Gly Leu Arg Pro Ala
                5
```

```
<210> SEQ ID NO 8
<211> LENGTH: 1104
<212> TYPE: DNA
<213> ORGANISM: Rhodotorula Gracilis

<400> SEQUENCE: 8 atg cac tct cag aag cgc gtc gtt gtc ctc gga tca ggc gtt              42
Met His Ser Gln Lys Arg Val Val Val Leu Gly Ser Gly Val
                5                   10
```

```
atc ggt ctg agc agc gcc ctc atc ctc gct cgg aag ggc tac         84
Ile Gly Leu Ser Ser Ala Leu Ile Leu Ala Arg Lys Gly Tyr
 15              20                  25 agc gtg cat att ctc gcg cgc gac ttg ccg gag gac gtc tcg        126
Ser Val His Ile Leu Ala Arg Asp Leu Pro Glu Asp Val Ser
         30                  35                  40 agc cag act ttc gct tca cca tgg gct ggc gcg aat tgg acg        168
Ser Gln Thr Phe Ala Ser Pro Trp Ala Gly Ala Asn Trp Thr
             45                  50                  55 cct ttc atg acg ctt aca gac ggt cct cga caa gca aaa tgg        210
Pro Phe Met Thr Leu Thr Asp Gly Pro Arg Gln Ala Lys Trp
                 60                  65                  70 gaa gaa tcg act ttc aag aag tgg gtc gag ttg gtc ccg acg        252
Glu Glu Ser Thr Phe Lys Lys Trp Val Glu Leu Val Pro Thr
                     75                  80 ggc cat gcc atg tgg ctc aag ggg acg agg cgg ttc gcg cag        294
Gly His Ala Met Trp Leu Lys Gly Thr Arg Arg Phe Ala Gln
 85                  90                  100 aac gaa gac ggc ttg ctc ggg cac tgg tac aag gac atc acg        336
Asn Glu Asp Gly Leu Leu Gly His Trp Tyr Lys Asp Ile Thr
105                 110                 115 cca aat tac cgc ccc ctc cca tct tcc gaa tgt cca cct ggc        378
Pro Asn Tyr Arg Pro Leu Pro Ser Ser Glu Cys Pro Pro Gly
        120                 125                 130 gct atc ggc gta acc tac gac acc ctc tcc gtc cac gca cca        420
Ala Ile Gly Val Thr Tyr Asp Thr Leu Ser Val His Ala Pro
            135                 140                 145 aag tac tgc cag tac ctt gca aga gag ctg cag aag ctc ggc        462
Lys Tyr Cys Gln Tyr Leu Ala Arg Glu Leu Gln Lys Leu Gly
                150                 155 gcg acg ttt gag aga cgg acc gtt acg tcg ctt gag cag gcg        504
Ala Thr Phe Glu Arg Arg Thr Val Thr Ser Leu Glu Gln Ala
160                 165                 170 ttc gac ggt gcg gat ttg gtg gtc aac gct acg gga ctt ggc        546
Phe Asp Gly Ala Asp Leu Val Val Asn Ala Thr Gly Leu Gly
        175                 180                 185 gcc aag tcg att gcg ggc atc gac gac caa gcc gcc gag cca        588
Ala Lys Ser Ile Ala Gly Ile Asp Asp Gln Ala Ala Glu Pro
            190                 195                 200 atc cgc ggc caa acc gtc ctc gtc aag tcc cca tgc aag cga        630
Ile Arg Gly Gln Thr Val Leu Val Lys Ser Pro Cys Lys Arg
                205                 210                 215 tgc acg atg gac tcg tcc gac ccc gct tct ccc gcc tac atc        672
Cys Thr Met Asp Ser Ser Asp Pro Ala Ser Pro Ala Tyr Ile
                    220                 225 att ccc cga cca ggt ggg gaa gtc atc tgc ggc ggg acg tac        714
Ile Pro Arg Pro Gly Gly Glu Val Ile Cys Gly Gly Thr Tyr
230                 235                 240 ggc gtg gga gac tgg gac ttg tct gtc aac cca gag acg gtc        756
Gly Val Gly Asp Trp Asp Leu Ser Val Asn Pro Glu Thr Val
        245                 250                 255 cag cgg atc ctc aag cac tgc ttg cgc ctc gac ccg acc atc        798
Gln Arg Ile Leu Lys His Cys Leu Arg Leu Asp Pro Thr Ile
            260                 265                 270 tcg agc gac gga acg atc gaa ggc atc gag gtc ctc cgc cac        840
Ser Ser Asp Gly Thr Ile Glu Gly Ile Glu Val Leu Arg His
                275                 280                 285 aac gtc ggc ttg cga cct gca cga cga ggc gga ccc cgc gtc        882
Asn Val Gly Leu Arg Pro Ala Arg Arg Gly Gly Pro Arg Val
```

| | | | | | | | | | | | |
|---|---|---|---|---|---|---|---|---|---|---|---|
| | | | | 290 | | | | 295 | | | |
| gag | gca | gaa | cgg | atc | gtc | ctg | cct | ctc | gac | cgg | aca | aag | tcg | 924 |
| Glu | Ala | Glu | Arg | Ile | Val | Leu | Pro | Leu | Asp | Arg | Thr | Lys | Ser | |
| 300 | | | | 305 | | | | 310 | | | | | | |

```
gag gca gaa cgg atc gtc ctg cct ctc gac cgg aca aag tcg      924
Glu Ala Glu Arg Ile Val Leu Pro Leu Asp Arg Thr Lys Ser
300             305             310 ccc ctc tcg ctc ggc agg ggc agc gca cga gcg gcg aag gag      966
Pro Leu Ser Leu Gly Arg Gly Ser Ala Arg Ala Ala Lys Glu
315             320             325 aag gag gtc acg ctt gtg cat gcg tat ggc ttc tcg agt gcg     1008
Lys Glu Val Thr Leu Val His Ala Tyr Gly Phe Ser Ser Ala
        330             335             340 gga tac cag cag agt tgg ggc gcg gcg gag gat gtc gcg cag     1050
Gly Tyr Gln Gln Ser Trp Gly Ala Ala Glu Asp Val Ala Gln
            345             350             355 ctc gtc gac gag gcg ttc cag cgg tac cac ggc gcg gcg cgg     1092
Leu Val Asp Glu Ala Phe Gln Arg Tyr His Gly Ala Ala Arg
                360             365 gag tcg aag ttg                                             1104
Glu Ser Lys Leu
370
```

<210> SEQ ID NO 9
<211> LENGTH: 368
<212> TYPE: PRT
<213> ORGANISM: Rhodotorula Gracilis

<400> SEQUENCE: 9

```
Met His Ser Gln Lys Arg Val Val Leu Gly Ser Gly Val
                5                  10

Ile Gly Leu Ser Ser Ala Leu Ile Leu Ala Arg Lys Gly Tyr
15                  20                  25

Ser Val His Ile Leu Ala Arg Asp Leu Pro Glu Asp Val Ser
        30                  35                  40

Ser Gln Thr Phe Ala Ser Pro Trp Ala Gly Ala Asn Trp Thr
            45                  50                  55

Pro Phe Met Thr Leu Thr Asp Gly Pro Arg Gln Ala Lys Trp
                60                  65                  70

Glu Glu Ser Thr Phe Lys Lys Trp Val Glu Leu Val Pro Thr
                    75                  80

Gly His Ala Met Trp Leu Lys Gly Thr Arg Arg Phe Ala Gln
85                  90                  95

Asn Glu Asp Gly Leu Leu Gly His Trp Tyr Lys Asp Ile Thr
    100                 105                 110

Pro Asn Tyr Arg Pro Leu Pro Ser Ser Glu Cys Pro Pro Gly
        115                 120                 125

Ala Ile Gly Val Thr Tyr Asp Thr Leu Ser Val His Ala Pro
            130                 135                 140

Lys Tyr Cys Gln Tyr Leu Ala Arg Glu Leu Gln Lys Leu Gly
                145                 150

Ala Thr Phe Glu Arg Arg Thr Val Thr Ser Leu Glu Gln Ala
155                 160                 165

Phe Asp Gly Ala Asp Leu Val Val Asn Ala Thr Gly Leu Gly
    170                 175                 180

Ala Lys Ser Ile Ala Gly Ile Asp Asp Gln Ala Ala Glu Pro
        185                 190                 195

Ile Arg Gly Gln Thr Val Leu Val Lys Ser Pro Cys Lys Arg
            200                 205                 210
```

-continued

```
Cys Thr Met Asp Ser Ser Asp Pro Ala Ser Pro Ala Tyr Ile
            215             220

Ile Pro Arg Pro Gly Gly Glu Val Ile Cys Gly Gly Thr Tyr
225             230             235

Gly Val Gly Asp Trp Asp Leu Ser Val Asn Pro Glu Thr Val
    240             245             250

Gln Arg Ile Leu Lys His Cys Leu Arg Leu Asp Pro Thr Ile
        255             260             265

Ser Ser Asp Gly Thr Ile Glu Gly Ile Glu Val Leu Arg His
            270             275             280

Asn Val Gly Leu Arg Pro Ala Arg Arg Gly Gly Pro Arg Val
                285             290

Glu Ala Glu Arg Ile Val Leu Pro Leu Asp Arg Thr Lys Ser
295             300             305

Pro Leu Ser Leu Gly Arg Gly Ser Ala Arg Ala Ala Lys Glu
        310             315             320

Lys Glu Val Thr Leu Val His Ala Tyr Gly Phe Ser Ser Ala
            325             330             335

Gly Tyr Gln Gln Ser Trp Gly Ala Ala Glu Asp Val Ala Gln
                340             345             350

Leu Val Asp Glu Ala Phe Gln Arg Tyr His Gly Ala Ala Arg
                355             360

Glu Ser Lys Leu
365
```